US009655822B2

(12) United States Patent
Perrier et al.

(10) Patent No.: US 9,655,822 B2
(45) Date of Patent: May 23, 2017

(54) HYDRATED LAMELLAR PHASES OR LIPOSOMES WHICH CONTAIN A FATTY MONOAMINE OR A CATIONIC POLYMER WHICH PROMOTES INTRACELLULAR PENETRATION, AND A COSMETIC OR PHARMACEUTICAL COMPOSITION CONTAINING SAME, AS WELL AS A METHOD OF SCREENING SUCH A SUBSTANCE

(75) Inventors: Eric Perrier, Les Cotes d'Arey (FR); Valerie Andre, Ampuis (FR); Isabelle Bonnet, Lyons (FR)

(73) Assignee: BASF Beauty Care Solutions France S.A.S., Lyons (FR)

(*) Notice: Subject to any disclaimer, the term of this patent is extended or adjusted under 35 U.S.C. 154(b) by 1808 days.

(21) Appl. No.: 10/880,810

(22) Filed: Jun. 30, 2004

(65) Prior Publication Data
US 2005/0266065 A1    Dec. 1, 2005

(30) Foreign Application Priority Data

May 25, 2004  (FR) ..................... 04 05640

(51) Int. Cl.

| | |
|---|---|
| *A61K 9/127* | (2006.01) |
| *A61K 8/14* | (2006.01) |
| *A61K 8/04* | (2006.01) |
| *A61K 8/41* | (2006.01) |
| *A61K 8/73* | (2006.01) |
| *A61K 8/81* | (2006.01) |
| *A61K 8/84* | (2006.01) |
| *A61K 8/97* | (2017.01) |
| *A61Q 5/06* | (2006.01) |
| *A61Q 19/00* | (2006.01) |
| *A61Q 19/04* | (2006.01) |
| *A61K 9/20* | (2006.01) |
| *A61Q 1/06* | (2006.01) |
| *A61Q 1/10* | (2006.01) |
| *A61Q 19/02* | (2006.01) |
| *A61Q 19/08* | (2006.01) |

(52) U.S. Cl.
CPC .................. *A61K 8/14* (2013.01); *A61K 8/04* (2013.01); *A61K 8/41* (2013.01); *A61K 8/73* (2013.01); *A61K 8/736* (2013.01); *A61K 8/8182* (2013.01); *A61K 8/84* (2013.01); *A61K 8/97* (2013.01); *A61K 9/1272* (2013.01); *A61Q 5/065* (2013.01); *A61Q 19/00* (2013.01); *A61Q 19/04* (2013.01); *A61K 9/2063* (2013.01); *A61K 2800/434* (2013.01); *A61K 2800/5426* (2013.01); *A61Q 1/06* (2013.01); *A61Q 1/10* (2013.01); *A61Q 19/02* (2013.01); *A61Q 19/08* (2013.01)

(58) Field of Classification Search
USPC ........................................................ 424/450
See application file for complete search history.

(56) References Cited

U.S. PATENT DOCUMENTS

| | | |
|---|---|---|
| 4,617,186 A | 10/1986 | Schäfer et al. |
| 4,721,612 A | 1/1988 | Janoff et al. |
| 4,921,644 A | 5/1990 | Lau et al. |
| 5,230,899 A | 7/1993 | Park et al. |
| 5,540,936 A * | 7/1996 | Coe et al. ................... 424/450 |
| 5,603,872 A * | 2/1997 | Margalit ....................... 264/4.3 |
| 5,610,201 A | 3/1997 | Grolier et al. ............... 514/773 |
| 5,807,097 A | 9/1998 | Döbbeling et al. |
| 5,807,957 A | 9/1998 | Samour et al. ................ 528/48 |
| 5,824,812 A | 10/1998 | Nantz et al. |
| 5,962,015 A | 10/1999 | Delrieu et al. .............. 424/450 |
| 6,071,535 A | 6/2000 | Hayward et al. |
| 6,083,491 A * | 7/2000 | Mellul et al. ................... 424/63 |
| 6,177,100 B1 * | 1/2001 | Grollier et al. .............. 424/450 |
| 6,277,401 B1 | 8/2001 | Bello et al. .................. 424/449 |
| 6,277,404 B1 | 8/2001 | Laversanne et al. |
| 6,696,038 B1 | 2/2004 | Mahato et al. |
| 2002/0001613 A1 * | 1/2002 | Niemiec et al. .............. 424/450 |
| 2002/0114829 A1 * | 8/2002 | Onyuksel et al. ............ 424/450 |
| 2003/0044407 A1 | 3/2003 | Chang et al. |
| 2003/0053974 A1 * | 3/2003 | Shefer et al. ............. 424/70.11 |
| 2003/0068364 A1 | 4/2003 | Garces et al. |
| 2003/0073619 A1 | 4/2003 | Mahato et al. |
| 2003/0223982 A1 * | 12/2003 | Schlotmann et al. ..... 424/94.61 |
| 2004/0062780 A1 | 4/2004 | Keller ........................... 424/401 |
| 2004/0234563 A1 * | 11/2004 | Bruening et al. ............ 424/401 |
| 2006/0078605 A1 * | 4/2006 | Mammarella ................ 424/450 |
| 2006/0110379 A1 * | 5/2006 | Green et al. ................. 424/94.5 |

FOREIGN PATENT DOCUMENTS

| | | |
|---|---|---|
| DE | 37 13 494 C2 | 4/1987 |
| DE | 39 35 257 A1 | 4/1991 |

(Continued)

OTHER PUBLICATIONS

Eytan, et al., "Cationic Amphiphiles Induce Fusion of Acidic Liposomes" *Biochimica et Biophysica Acta*, 1984, vol. 778, pp. 38-48.

(Continued)

*Primary Examiner* — Gollamudi Kishore
(74) *Attorney, Agent, or Firm* — Drinker Biddle & Reath LLP

(57) ABSTRACT

The invention relates to novel hydrated lamellar phases or liposomes which contain either polyethylenimine, or a substance which stimulates intracellular penetration selected from the group consisting of:

i) a fatty monoamine of carbon-containing chain length of between C10 and C18;

ii) a cationic polymer, optionally at least one fluorescent compound which is essentially inert with respect to the intracellular penetration, which enables this penetration to be visualised.

These liposomes are very useful in cosmetics or in pharmacy for stimulating the intracellular penetration of a substance or active principle.

29 Claims, 1 Drawing Sheet

(56) References Cited

FOREIGN PATENT DOCUMENTS

| | | | |
|---|---|---|---|
| EP | 0 198 765 | 10/1986 | |
| EP | 0 992 236 A1 | 4/2000 | |
| EP | 1 323 415 A1 | 10/2001 | |
| EP | 1 304 160 A1 | 10/2002 | |
| FR | 2 662 605 | 12/1991 | |
| GB | 2 198 947 | 2/1990 | |
| JP | 2002-500630 | 1/2002 | ............. A61K 7/075 |
| WO | WO 87/06499 | 11/1987 | ............. B01J 13/02 |
| WO | WO 89/07937 | 9/1989 | ............. A61K 9/52 |
| WO | WO 96/31196 | 10/1996 | ............. A61K 9/127 |
| WO | 98/46199 | 10/1998 | |
| WO | 00/03683 | 1/2000 | |
| WO | 00/53230 | 9/2000 | |
| WO | 00/62813 A3 | 10/2000 | |
| WO | 00/73471 A1 | 12/2000 | |
| WO | WO 01/72264 | 10/2001 | ............. A61K 7/00 |
| WO | 02/060412 A3 | 8/2002 | |
| WO | 02/076491 A1 | 10/2002 | |
| WO | 03/038103 A1 | 5/2003 | |
| WO | 2004/002454 | 1/2004 | |
| WO | WO 2004/006882 | 1/2004 | |
| WO | 2004/030654 A1 | 4/2004 | |
| WO | WO 2004/028495 | 4/2004 | ............. A61K 7/50 |
| WO | 2004/041298 | 5/2004 | ............. A61K 7/06 |

OTHER PUBLICATIONS

Takeuchi et al., "Destabilization of Whole Skin Lipid Bio-liposomes Induced by Skin Penetration Enhancers and FT-IR/ATR (Fourier Transform Infrared/Atteniated Total Reflection) Analysis of Stratum Corneum Lipids" *Chem. Pharm.*, 1992, vol. 40, No. 2, pp. 484-487.

Nalecz, et al., "Effect of Phospholipid Composition on the Surface Potential of Liposomes and the Activity of Enzymes Incorporated into Liposomes" *Eur. J. Biochem,* 1980, vol. 112, pp. 75-80.

Xiangyang Shi, et al., The aggregation behavior of collagen in aqueous solution and its property of stablizing liposomes in vitro, Mar. 18, 1998, Biomaterials 22 (2001) 1627-1634.

Chien-Hsin Lee, et al., Synergistic effect of polyethylenimine and cationic liposomes in nucleic acid delivery to human cancer cells, Oct. 29, 2002, Biochimica et Biophysica Acta 1611 (2003) 55-62.

Patent Abstract of Japan, abstracting JP 06-178116.

X.Shi et al., "The Aggregation Behavior of Collagen in Aqueous Solution and its Property of Stabilizing Liposomes in Vitro" Biomaterials/ 22 (2001) pp. 1627-1634.

Lee, et al., "Synergistic effect of polyethylenimine and cationic liposomes in nucleic acid delivery to human cancer cells" *Biochimica et Biophysica Acta,* 2003, vol. 1611, pp. 55-62.

* cited by examiner

HYDRATED LAMELLAR PHASES OR LIPOSOMES WHICH CONTAIN A FATTY MONOAMINE OR A CATIONIC POLYMER WHICH PROMOTES INTRACELLULAR PENETRATION, AND A COSMETIC OR PHARMACEUTICAL COMPOSITION CONTAINING SAME, AS WELL AS A METHOD OF SCREENING SUCH A SUBSTANCE

The invention relates essentially to hydrated lamellar phases or liposomes which contain a substance which promotes the intracellular penetration of a substance or active principle which is carried by said hydrated lamellar phase or the liposomes. More specifically, the invention relates to hydrated lamellar phases or liposomes which comprise, at least in part in their structure, a substance or a mixture of substances capable of stimulating the intracellular penetration of at least one active principle which is present or carried in said hydrated lamellar phase or liposome, selected from the group which consists either of polyethylenimine, or of a fatty monoamine of carbon-containing chain length of between C10 and C18, defined in the present description and the claims, or of a cationic polymer also defined in the present description and the claims, optionally containing a fluorescent compound which is essentially inert with respect to the intracellular penetration, for example pentafluorobenzoylamine fluorescein, which enables this penetration to be visualised, notably in the context of a method of screening a substance which is potentially active for promoting the intracellular penetration.

The invention also relates to cosmetic or dermocosmetic compositions, or pharmaceutical or dermopharmaceutical compositions which contain such hydrated lamellar phases or liposomes.

The invention also relates to a method of cosmetic care comprising applying a cosmetic or dermocosmetic composition according to the invention onto the zones of the skin or of the hair concerned. The invention also relates to the use of hydrated lamellar phases or liposomes as cosmetic agents notably for the manufacture of a cosmetic composition notably for an anti-wrinkle activity, an anti-oxidant activity, a slimming activity, a skin paling activity, a skin or hair pigmenting activity, according to the nature of the substance or active principle which is present or carried in the hydrated lamellar phases or the liposomes.

The invention further relates to a method of screening for detecting substances which is potentially active for promoting the intracellular penetration.

STATE OF THE ART

Recently, cationic liposomes, called CATESOMES™ have been described in the document U.S. Pat. No. 6,071,535 (Hayward), which are very sensitive both to the pH and to the ionic strength of the surrounding medium, and which are constituted of $N_n,N_n$-dimethyl-1,n-diamino alkyl type diamine fatty alkyl ammonium fatty acyl salts, the diamine being designated DDA, the alkyl part having a number of carbon atoms n of between 2 and 8 (see column 5, lines 37 to 39), the fatty acylated part is provided by a fatty acid having 10 to 30 carbon atoms in order to form a substance designated ADDA (column 5, lines 41 to 48).

Such ADDA substances are said to be commercially available under the commercial name CATEMOL from the company Phoenix Chemical, Somerville, N.J., USA, reference CATEMOL 220 and 260.

The CATESOMES are formed by combining a fatty acid having 10 to 28 carbon atoms, for example, behenic acid, in order to form salts called A-ADDA salts, the mixture being made in an equimolar proportion and at a pH of between 6 and 10, in order to form a salt between the quaternary amine group of the ADDA substance and the carboxyl group of the fatty acid (see column 5, line 66 to column 6, line 4).

This Hayward document also cites the document U.S. Pat. No. 4,721,612, which relates to conventional liposomes, the bilayers of which comprise a salt form of a sterol and of an organic acid, such as the tris-salt form of a sterol hemisuccinate (column 5, lines 13 to 18).

SUMMARY OF THE INVENTION

A main aim of the present invention is to solve, in an unexpected manner, the novel technical problem which consists in providing novel hydrated lamellar phases or liposomes which enable an increase in the intracellular penetration of a substance or active principle, advantageously in the cells of the skin or of the hair, while at the same time limiting the cytotoxicity or the induction of cell death of said cells.

A further main aim of the present invention is to solve, in an unexpected manner, the technical problem of providing novel hydrated lamellar phases or liposomes which not only promote the intracellular penetration of a substance or active principle, advantageously in cells of the skin or of the hair, but which enable a relatively high rate of encapsulation of said substance or active principle to be obtained in said hydrated lamellar phases or the liposomes.

A further main aim of the present invention is to solve, in an unexpected manner, the novel technical problem which consists in providing novel cosmetic or dermocosmetic, pharmaceutical or dermopharmaceutical compositions, which contain hydrated lamellar phases or liposomes which possess an excellent intracellular penetration of a substance or active principle, advantageously in cells of the skin or of the hair, while at the same time limiting the cytotoxicity or the induction of cell death (or apoptosis) of said cells.

A further main aim of the present invention is to solve, in an unexpected manner, a novel technical problem which consists in providing a novel method of screening a substance which is potentially active for improving the intracellular penetration of a substance or active principle, advantageously in cells of the skin or of the hair and preferably also for evaluating the cytotoxicity or the induction of apoptosis of said cells.

The whole of these technical problems is solved for the first time simultaneously, in a safe and reliable manner, which can be used on a cosmetic or pharmaceutical and industrial scale.

Thus, according to a first aspect, the present invention provides hydrated lamellar phases or liposomes, characterised in that they comprise at least in part in their structure, a substance or a mixture of substances which is (are) capable of stimulating the intracellular penetration of at least one active principle which is present or carried in said hydrated lamellar phases or liposomes, and which is (are) selected from the group consisting of:
a) polyethylenimine;
b) a primary, secondary, tertiary or quaternary fatty monoamine of carbon-containing chain length of between C10 and C18, advantageously a monoamine comprising a single C10-C18 fatty chain, preferably a primary or quaternary monoamine comprising a single C10-C18 fatty chain;

c) a cationic polymer, particularly a cationic natural polymer or optionally rendered cationic, or a cationic synthetic polymer, said lamellar phases or liposomes optionally containing at least one fluorescent compound which is essentially inert with respect to the intracellular penetration, for example pentafluorobenzoylamino fluorescein, which enables this penetration to be visualised.

According to a particular embodiment, said lamellar phases or liposomes are characterised in that the optionally cationic natural polymer is selected from the group consisting of chitosan, quaternised honey polymer; plant proteins, particularly wheat proteins or quaternised wheat proteins, rice proteins or quaternised rice proteins, soya proteins or quaternised soya proteins; collagen or quaternised collagen, keratin or quaternised keratin, casein or quaternised casein, cellulose or quaternised cellulose, guar or quaternised guar. These quaternised polymers are generally commercial products, and the quaternisation is generally obtained by grafting of tertiary amines onto the chemical groups of the initial polymer.

According to another advantageous embodiment, said lamellar phases or liposomes are characterised in that the primary monoamine is selected from the group consisting of decylamine, undecylamine, dodecylamine, tridecylamine, tetradecylamine, pentadecylamine, octadecylamine, or is a mixture of primary amines such as mixtures of copra amines having a hydrocarbon chain of between C8 and C18.

According to a particular embodiment, the lamellar phases or liposomes contain polyethylenimine.

According to another particular embodiment, the lamellar phases or the liposomes comprise, in the lipid phase, at least one agent which modifies the membrane of liposomes, for example a polar lipid selected from the group consisting of a triglyceride, of a polar phospholipid or of a polar sphingolipid, alone or in a mixture.

According to another particular embodiment, the polar phospholipid mentioned above is selected from phosphatidylcholine or lecithin, phosphatidylethanolamine or cephaline, phosphatidylserine, phosphatidylglycerol, diphosphatidylglycerol or cardiolipine, phosphatidylinositol, alone or in a mixture.

Advantageously, this polar phospholipid is selected from a ceramide, a sphingophospholipid, a glycosphyngolipid alone or in a mixture.

According to another variant, the lamellar phases or liposomes comprise at least one polar lipid or a polar sphingolipid, particularly in the form of a salt of an organic acid of a sterol such as the tris-sel of a sterol hemisuccinate.

According to another advantageous embodiment of the invention, the lamellar phases or liposomes comprise at least one lecithin, in the lipid phase, extracted from a natural source selected from the group consisting of soya, rape, sunflower, lupin, groundnut, sesame, marrow, bran oil, bigseed falseflax, calendula, flax and hemp, alone or in a mixture.

According to another variant, the lamellar phases or the liposomes can also comprise a lipid phase which contains cholesterol or a derivative of cholesterol, such as cholesterol hemisuccinate, as agent which rigidifies the membranes.

According to another advantageous embodiment of the invention, the lamellar phases or the liposomes can comprise, in the lipid phase, at least one surfactant agent or surfactant, as agent which fluidifies the lamellar phase or the membranes of the liposomes.

According to another particular embodiment of the invention, the lamellar phases or liposomes contain a fluorescent agent which is essentially inert with respect to the intracellular penetration, particularly the intracellular penetration of the skin or of the hair, of which a currently preferred example of such a fluorescent agent comprises or is constituted of 5-pentafluorobenzoyl-aminefluorecein, particularly at a proportion of about 0.01% by weight of the composition which contains said lamellar phase or liposomes.

According to an advantageous embodiment of the invention, the concentration of substance(s) which stimulate(s) the intracellular penetration is between 0.05% and 25% by weight of the composition which contains the hydrated lamellar phases or the liposomes, preferably between 0.5% and 2.5% by weight of said composition.

According to yet another advantageous embodiment of the invention, the fatty monoamine mentioned above has a carbon-containing chain length of between C10 and C13. Advantageously, the fatty monoamine mentioned above is a quaternised primary monoamine comprising a single fatty carbon-containing chain of between C10 and C18, preferably between C10 and C13.

According to yet another advantageous embodiment of the invention, the quaternised molecule which promotes the intracellular penetration of the active principles is selected from a solution of quaternised plant proteins, preferably of soya proteins, which are quaternised of formula of R—N($R_1R_2R_3$) type, in which R symbolises the plant protein molecule, which is hydrolysed or not, hydroxyalkylated, particularly hydroxypropylated, or not; $R_1$ and $R_2$ independently being a $C_1$-$C_6$ hydrocarbon group, preferably methyl or ethyl, and $R_3$ being an alkyl radical having 10 to 18 carbon atoms, and preferably mainly 12 carbon atoms (lauryl).

According to another embodiment of the invention, the substance or active principle which is present or carried in the hydrated lamellar phases or the liposomes is selected from the group consisting of an anti-radical agent such as vitamin E, a flavonoid, a carotenoid, vitamin C, or their derivatives; a depigmenting agent such as catechin, hydroquinone, arbutin, phytic acid, ellagic acid, vitamin C, or their derivatives; a slimming agent such as at least one xanthine, a skin or hair pigmenting agent such as tyrosine, tryptophan, phenylalanine, a Coleus extract or their derivatives.

According to a second aspect, the present invention also relates to cosmetic or dermocosmetic compositions; pharmaceutical or dermopharmaceutical compositions, comprising such hydrated lamellar phases or liposomes which comprise at least one substance which stimulates the intracellular penetration, optionally in a cosmetically, dermocosmetically, pharmaceutically or dermopharmaceutically acceptable excipient.

Such excipients are well known to the person skilled in the art, and some are cited in the two prior art documents indicated in the description of the prior art.

Other excipients result from the examples of cosmetic, dermocosmetic, pharmaceutical or dermopharmaceutical compositions of the following description, which is given simply as an illustration and which in no way limits the scope of the invention.

According to a third aspect, the invention also relates to a method of cosmetic care comprising topically applying, onto the skin or the hair, a composition comprising hydrated lamellar phases or liposomes as described above, or as resulting from the following description, which is made in relation to the Examples which make up an integral part of the invention.

According to a fourth aspect, the present invention also covers a method of therapeutic treatment, characterised in that it comprises topically applying, onto the skin or the hair, a composition comprising hydrated lamellar phases or liposomes as described above or as resulting from the Examples which make up an integral part of the invention, in an amount which is sufficient to make the therapeutic treatment sought after. In general, the hydrated lamellar phases or the liposomes comprise at least one active principle which is present or carried in said hydrated lamellar phases or the liposomes having an activity which is linked to the therapeutic treatment sought after.

In the context of a cosmetic care, the present invention provides carrying out a cosmetic care selected from the group consisting of an anti-wrinkle care, an anti-oxidant care, a slimming care, a skin paling care, a skin or hair pigmenting care.

In the context of a therapeutic treatment, the invention provides carrying out an appropriate therapeutic treatment of the skin or of the hair, as a function of the pathology to be treated.

The invention also relates to the use of hydrated lamellar phases or liposomes as cosmetic agents, notably for the manufacture of a cosmetic composition notably for an anti-wrinkle activity, an anti-oxidant activity, a slimming activity, a skin paling activity, a skin or hair pigmenting activity, or for the manufacture of a pharmaceutical composition, in each of the cases, preferably via the topical route.

According to a fifth aspect, the present invention also relates to a method of screening of at least one substance which is potentially capable of stimulating the intracellular penetration of a substance or active principle which is carried by hydrated lamellar phases or liposomes, characterised in that it comprises:
a) preparing a hydro-lipidic mixture which is capable of forming said hydrated lamellar phases or said liposomes;
b) incorporating, before the dispersing process in this hydro-lipidic mixture, a fluorescent compound, which is preferably essentially inert with respect to the intracellular penetration;
c) optionally incorporating, before or during the process of dispersion in the hydro-lipidic mixture, a test substance selected from said substance which is potentially active, which is capable of stimulating the intracellular penetration, and a reference substance;
d) preparing said hydrated lamellar phases or said liposomes according to any suitable method of forming said hydrated lamellar phases or liposomes from the hydro-lipidic mixture as obtained either in step b) or in step c) above;
e) detecting at least the intracellular penetration of the fluorescent compound by measurement of the intracellular fluorescence.

According to another embodiment, the result of the intracellular penetration of the fluorescent compound is compared with the intracellular penetration obtained with a reference substance, particularly comprising polyethylenimine.

According to yet another embodiment, the cytotoxicity and/or the induction of apoptosis of the substance which is potentially active is measured, notably on fibroblasts, preferably normal human fibroblasts, in culture.

According to yet another embodiment, the fluorescent compound which is essentially inert with respect to the intracellular penetration is a fluorescent compound which does not penetrate spontaneously into said fibroblast in culture.

According to yet another embodiment, the fluorescent compound comprises, or is, pentafluorobenzoylaminofluorescein which is used at a concentration of 0.01% by weight of the final composition which contains the hydrated lamellar phases or the liposomes which are used for evaluating the intracellular penetration.

According to another advantageous embodiment of the method, the fluorescent compound is incorporated in the presence of polyethylenimine, the fluorescent compound and the polyethylenimine being at a non-cytotoxic concentration.

According to yet another advantageous embodiment of the invention, the substance which is potentially capable of stimulating the intracellular penetration is selected from a primary fatty monoamine of alkyl chain length of between C10 and C18, preferably between C10 and 13, or a cationic polymer, particularly a natural polymer which is optionally rendered cationic, or a cationic synthetic polymer which is incorporated in the lamellar phases or liposomes, as defined above or in the following description with reference to the Examples, which make up an integral part of the invention.

The invention further relates, according to a sixth aspect, to the use of hydrated lamellar phases or liposomes as described above or as resulting from the Examples making up an integral part of the invention, as a cosmetic agent or for the manufacture of a cosmetic composition and notably for an anti-wrinkle activity, an antioxidant activity, a slimming activity, a skin paling activity, a skin or hair pigmenting activity.

Within the context of any one of the preceding aspects, surfactants can advantageously be added to the hydro-lipidic mixture, so as to fluidify the membranes of the liposomes.

The present invention has necessitated the selection of a fluorescent tracer which does not penetrate spontaneously into the fibroblasts in culture for example, and which induces very little cytotoxicity by itself or after encapsulation in a liposome, is incorporated with a good yield in the liposomes based on soya lecithin for example (about 80%), and is stable after encapsulation (no release and change of fluorescence), and which does not induce an instability of the liposomes. The tracer selected is advantageously 5-pentafluorobenzoylaminofluorescein or PFB-F at a concentration at 0.01%, i.e. 185 µM final.

Advantageously, said methods of dispersion for preparing the liposomes are preferably selected from shearing, ultrasound, extrusion, hydration/dehydration (lyophilisation), freezing/thawing, reverse phase evaporation.

The presence of liposome (lamellar structure) is attested by transmission electronic microscopy. The size of the liposomes is evaluated by transmission electronic microscopy and laser particle size analysis.

Advantageously, the preparation of the liposomes is done at a pH of between 4 and 8, preferably at pH 6.

Advantageously, the intracellular penetration of an active principle sought after is in cells of the skin.

Advantageously, the intracellular penetration of an active principle in the cells of the skin mainly targets fibroblasts, keratinocytes and melanocytes.

The means of detection of the intracellular penetration are selected from the methods of quantification and of visualisation, and are preferably the quantification of the intensity of fluorescence by spectrofluorometry and epifluorescence optical microscopy visualisation.

Advantageously, molecules are considered to be efficient which firstly enable a stimulation of the intracellular penetration of the fluorescent tracer to be obtained at more than 10% greater than the negative control not containing any cationic molecule, advantageously equivalent or greater than the positive control which contains a reference cationic molecule, polyethylenimine, which is used at 50 μM. Secondly, the molecules selected must preferably not induce cytotoxic and/or apoptotic phenomena, or induce cytotoxic and/or apoptotic phenomena less than those of the reference cationic molecule (polyethylenimine used at 50 μM).

Advantageously, the active molecules selected for stimulating the intracellular penetration are selected from the group which consists of:
a) a primary to quaternary amine, of variable carbon-containing chain length, and advantageously decylamine, undecylamine, dodecylamine, tridecylamine, tetradecylamine, pentadecylamine, octadecylamine, benzyldimethyl (octadecyl) ammonium chloride (or stearylalkonium chloride), a mixture of primary amines (for example C8 to C18 copra amines), polyquaternium 16;
b) a cationic polymer and advantageously chitosan, or quaternised honey, plant proteins, particularly wheat proteins, rice proteins, soya proteins or their quaternised derivatives; quaternised cellulose or guar.

Advantageously, the concentrations of cationic agents used are between 0.05% and 25%, preferably between 0.5 and 2.5%, preferably 1%.

Advantageously, the stimulation of the intracellular penetration is optimal for carbon-containing chains of medium length (C10 to C13), average for chains of long length (C15 to C18) and less for short chains (less than C10).

Advantageously, the stimulation of the intracellular penetration is optimal for a primary amine (e.g. C10-NH2) in comparison to a secondary amine comprising the same two carbon-containing chains for example (C10-NH—C10), due to the steric hindrance induced.

Advantageously, certain quaternised polymers enable a better factor of stimulation of the intracellular penetration to be obtained by the very nature of the polymer selected, e.g. lauryldimonium hydroxypropyl hydrolysed wheat protein is about 6 times less efficient than lauryldimonium hydroxypropyl hydrolysed soya protein.

Advantageously, the cationic molecules selected are less cytotoxic and/or induce less apoptosis than the reference molecule used, polyethylenimine, used at 50 μM.

Advantageously, the quantification of the cytotoxicity is done with a cell viability test which evaluates the cell alkaline phosphatase activity, and an interleukin 1 alpha determination. The apoptosis is evaluated by the quantification of caspase-1.

Advantageously, the liposomes prepared according to the innovative method described above are used in order to induce an increase of the intracellular penetration of cosmetic, dermocosmetic or pharmaceutical active principles, which are used in substitution of the fluorescent tracer.

Other aims, features and advantages of the invention will appear clearly to the person skilled in the art upon reading the explanatory description which makes reference to the following Examples.

The Examples make up an integral part of the present invention and any feature appearing novel with respect to any prior state of the art from the description taken in its entirety, including the Examples, makes up an integral part of the invention in its function and in its generality.

Thus, every Example is of general scope.

Furthermore, in the Examples, all the percentages are given by weight, unless indicated otherwise, the temperature is expressed in degrees Celsius unless indicated otherwise, and the pressure is atmospheric pressure, unless indicated otherwise.

DESCRIPTION OF THE FIGURES

Annexed

FIG. 1 represents fibroblasts which are incubated for 24 hours with liposomes having 0.01% of PBF-F with an enlargement of the objective multiplied by 10.

FIG. 2 represents fibroblasts which are incubated for 24 hours with liposomes having 0.01% of PBF-F with an enlargement of the objective multiplied by 40.

FIG. 3 represents fibroblasts which are incubated for 24 hours with liposomes having 0.01% of TRITC with an enlargement of the objective multiplied by 100.

FIG. 4 represents fibroblasts which are incubated for 24 hours with liposomes having 0.01% of TRITC and 3% of PEI, with an enlargement of the objective multiplied by 100.

EXAMPLE 1

Figure 1:
FIGS. 1 to 4 show the visualisation of the intracellular penetration of two pre-selected tracers according to the invention, PBF-F and TRITC, respectively.

Preparation and Purification of Liposome Encapsulating a Fluorescent Tracer

Fluorescent tracers not only have the advantage of being securing with regard to radioactivity for example, but are furthermore very simple to use when it is a question of making a quantification and of demonstrating a visual aspect of the intracellular penetration on cell culture models.

The selection of the tracer necessitated the preparation of liposomes which contain 0.01% of various hydrosoluble or liposoluble tracers, and their purification so as to remove the non-incorporated tracer before their application onto normal human fibroblasts. A liposome control is made in parallel without fluorescent tracer.

a) Selection of the Liposome Preparation Protocol

Liposomes are prepared with a concentration of 20% of soya lecithin dissolved in Trizma dilution buffer (Sigma, France) 55 mM-27 mM NaCl adjusted to pH 5. After magnetic agitation for 30 minutes at ambient temperature, the mixture is very vigorously homogenised for 10 minutes.

The liposomes are then diluted in DF medium [DMEM (Dulbecco's Modified Eagle's Medium)/Ham F12 glutamax 50/50 volume/volume, supplemented with 10% of calf serum, with penicillin at a final concentration of 100 UI/millilitre, with gentamicin at a final concentration of 1 microgram/millilitre, with amphotericin B at a final concentration of 1 microgram/millilitre] so as to obtain varying soya lecithin concentrations (0.5-1-2-3-4-5-7.5-10%).

250 μl of liposomal suspension is added onto cultures of normal human fibroblasts extracted from abdominal plasy and cultivated in a 96-well plate. Each concentration is tested on 6 different wells. The cell viability is evaluated by a test with paranitrophenylphosphate which determines the intracellular alkaline phosphatase activity after three rinses with pH 7.4 phosphate buffer. The percentage of living cells is calculated with respect to a control made without the addition of liposome in the culture well (n=6).

The results obtained show that a cell viability of more than 85% is obtained up to 7.5% of lecithin. At 10% of lecithin, the viability passes below the acceptable threshold of 75% viability.

The concentration of 5% which enables a cell viability of greater than 90% to be obtained is selected.

b) Preparation of 5% Soya Lecithin Liposome Incorporating a Fluorescent Tracer 0.5 g of soya lecithin, 0.01% of fluorescent tracer which is pre-solubilised according to the recommendations of the provider, are introduced into a dish and is diluted in 10 ml of Trizma buffer. After magnetic agitation for 30 minutes at ambient temperature, the mixture is vigorously homogenised for 10 minutes, in thus obtaining a liposomal solution in which the liposomes have an average size which can vary between 100 and 800 nanometres according to the exact conditions of homogenisation.

The aim of the purification step is to separate the non-encapsulated tracer fraction from the fraction of tracer which is encapsulated in the liposomes. For this, the liposomal solution is centrifuged in a conical tube for 10 minutes at 1,790 g at ambient temperature. The plugs are then recovered and then solubilised in 10 ml of culture medium.

The liposome negative control is made according to the protocol described above, without fluorescent tracer.

The samples are preserved for 24 hours at 4° C. in the absence of light. 26 series of liposomes are made with various types of fluorescent tracers, pH sensitive ones, calcium-sensitive ones, or others.

EXAMPLE 2

Selection of a Fluorescent Tracer which can be Encapsulated in a Liposome, which does not Penetrate Spontaneously in Normal Human Fibroblasts in Culture The selection of the tracer necessitated the preparation and the purification of liposomes, according to the protocol described in Example 1, these liposomes containing varying concentrations of the various hydrosoluble or liposoluble tracers (Table 1, Annex 1). The controls—a free fluorescent tracer—are made by dissolution at the same concentration of fluorescent tracer in the dilution buffer, so as to quantify its cytotoxicty and its spontaneous penetration in the fibroblasts.

The comparison with a liposome which does not contain any fluorescent tracer as negative control is made in parallel.

Practically, after extraction from a biopsy originating from abdominal plastic surgery, the fibroblasts are amplified in DF medium, i.e.: DMEM (Dulbecco's Modified Eagle's Medium)/Ham F12 glutamax 50/50 volume/volume, supplemented with 10% of calf serum, with penicillin at a final concentration of 100 UI/millilitre, with gentamicin at a final concentration of 1 microgram/millilitre, with amphotericin B at a final concentration of 1 microgram/millilitre.

Firstly, after centrifugation, the purified liposomes are taken up into DF culture medium, homogenised in a vortex, and are deposited at the rate of 1 ml per well on the fibroblasts cultivated in 24-well plates (Costar MW24). The controls are made under the same conditions. A non-treated control is also made.

The fibroblasts are incubated for 24 hours at 37° C. in the presence of the liposomes, and are then rinsed 3 times in pH 7.4 phosphate buffer. First of all, the fluorescence is evaluated dry by spectrofluorimetry with a Cytofluor 4000® (Millipore). Secondly, the intracellular fluorescence is observed for the molecules of interest on an Olympus® reverse microscope (IX70) by using the corresponding excitation filter (objective ×10, ×40 and ×100). Finally, the cytotoxicity of the fluorescent tracers is evaluated in a 96-well plate by incubation for 24 hours as described in Example 1.

The results obtained show that from the 25 molecules tested, only pentafluorobenzoylaminofluorescein PFB-F (P12925 Molecular Probes) and tetramethylrhodamine isothiocyanate TRITC (T-490 Molecular Probes) give interesting positive results after incorporation in a liposome, application on the fibroblasts for 24 hours and quantification of the penetration of the liposomal content.

Figure 2:
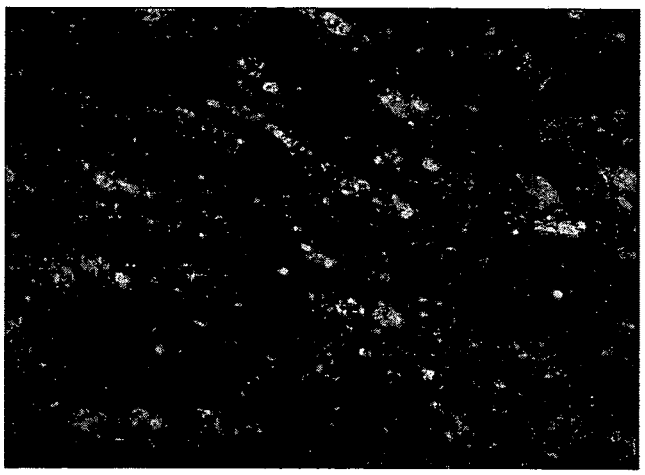
Figure 3:
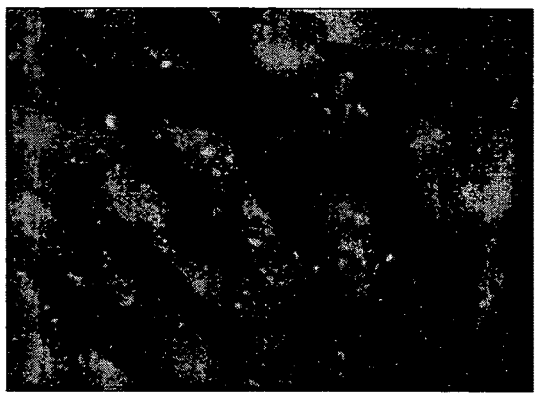
Figure 4:
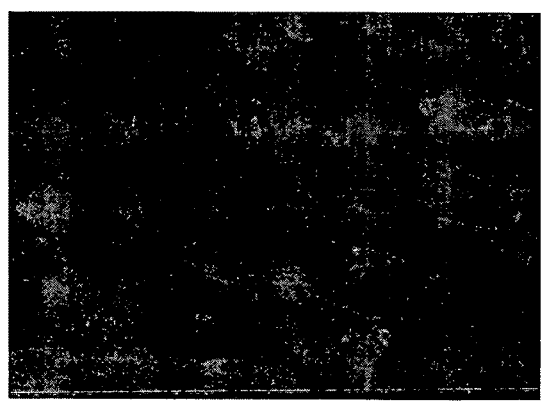

Annexed FIGS. 1 to 4 are photographs which visualise the intracellular penetration of the two pre-selected tracers PFB-F and TRITC at the concentration of 0.01% in liposomes after incubation with the fibroblasts for 24 hours.

TABLE 2

| | Results of the tracer screening | | |
|---|---|---|---|
| | Cytotoxicity (% of the non-treated control) | Penetration free probe | Penetration (fluorescence after washing) |
| PFB-F (485–530) | 110.7% | 8 (gain 45) | 65 (gain 45) |
| TRITC (530–620) | 74.8 | 295 (gain 50) | 1,119 (gain 50) |

However, although the TRITC gives a more intense marking, (Table 1 and Annexed FIGS. 1 to 4), it is nevertheless slightly cyctotoxic, it penetrates slightly when it is added free in the culture medium. PFB-F thus seems to be a better tracer.

EXAMPLE 3

Study of the Intracellular Penetration in the Presence of PFB-F (Pentafluorobenzoylaminofluorescein) or TRITC (Tetramethylrhodamine Isothiocyanate) in the Presence or not of Polyethylenimine The intracellular penetration of liposomes which contain 5% of soya lecithin, 0.01% of PFB-F or TRITC in the presence or not of 0.5% 25 kDa polyethylenimine (PEI), which are prepared according to the protocol described in Example 1, is analysed after incubation for 24 hours on human fibroblasts cultivated in a 24-well plate, as described in Example 2.

The results obtained show that the addition of PEI stimulates the penetration of the PFB-F liposomes 13.7 times, whereas the addition of PEI decreases the penetration of the TRITC liposomes 16 times (cf. photographs of Annexed FIGS. 1 to 4).

The tracer retained is therefore PFB-F or pentafluorobenzoylaminofluorescein at 0.01% in the liposome.

EXAMPLE 4

Study of the Stability of the Liposomes Containing Pentafluorobenzoylaminofluorescein (PFB-F)

The stability of the liposomes is analysed by study of the release of the fluorescent tracer into the DF culture medium by spectrofluorimetry; this study is made as a function of the pH, of the ionic strength and of the presence of detergent.

Practically, liposomes which contain 5% of soya lecithin, 0.01% of PFB-F and 50 µM of 25 kDa PEI are prepared. The liposomal solutions are adjusted to pH 6-7-8-9; the concentration of sodium chloride (NaCl) is adjusted to 50-100-150-200 mM and the concentration of sodium dodecyl sulphate (SDS) or Triton X-100 is adjusted to 0.1-0.5-1-3%. The results obtained are presented in Table 3.

TABLE 3

Study of the release as a function of the presence of detergents, of the ionic strength and of the pH.

| Molecules | Concentrations | Release: average | Release: Standard deviation |
|---|---|---|---|
| Triton X-100 | 3% | 44027 | 177 |
| | 1% | 45800 | 2888 |
| | 0.5% | 40834 | 39 |
| | 0.1% | 19829 | 103 |
| SDS | 3% | 62481 | 180 |
| | 1% | 71809 | 1558 |
| | 0.5% | 76676 | 200 |
| | 0.1% | 22990 | 108 |
| NaCl | 200 mM | 68527 | 2040 |
| | 150 mM | 7622 | 36 |
| | 100 mM | 6314 | 113 |
| | 50 mM | 5680 | 62 |
| pH | 9 | 25265 | 411 |
| | 8 | 18816 | 226 |
| | 7 | 8781 | 70 |
| | 6 | 7640 | 55 |

The results seem to indicate that the liposomes containing 50 µM of 25 kDa PEI start to destabilise from 200 mM NaCl, 0.5% of Triton X-100 or SDS and above pH 7.

EXAMPLE 5

Yield of Encapsulation of the Fluorescent Tracer PFB-B as a Function of the Concentration of Polyethylenimine Liposomes are prepared according to the method described in Example 5 with increasing concentrations of 25 kDa PEI from 0 to 100 µM. After centrifugation at 1,790 g for 10 minutes, the supernatants are quantified by spectrofluorimetry. The yields of encapsulation are calculated with respect to the initial concentration. The results are given in Table 4.

TABLE 4

Yield of encapsulation of PFB-F as a function of the concentration of PEI

| | Concentration of PEI (µM) | | | | |
|---|---|---|---|---|---|
| | 0 | 1 | 10 | 50 | 100 |
| Yield (%) | 89.0 | 92.3 | 91.0 | 87.5 | 86.3 |

It is noted that the yield of encapsulation is not affected by the increase in concentration of PEI.

EXAMPLE 6

Development of the Screening Conditions with Fluorescent Liposomes Containing Varying Concentrations of Polyethylenimine Liposomes are prepared according to the protocol described in Example 1 with varying concentrations of polyethylenimine (25 kDa PEI—neutralised by 6N hydrochloric acid), i.e. 0-5-10-50 µM and 0.01% of PFB-F.

The quantification is carried out by spectrofluorometry after incubation on fibroblasts cultivated in a monolayer in a 24-well plate for 2-4-6-24 and 48 hours after 3 washings in pH 7.4 phosphate buffer, against a non-treated fibroblasts blank and after normalisation against free PFB-F at the same concentration. The results are given in Table 5.

TABLE 5

Study of the intracellular penetration of the PFB-F as a function of time and the concentration of PEI (n = 4 for each condition), expressed in arbitrary units of fluorescence.

| | Concentration of PEI | | | | | | | |
|---|---|---|---|---|---|---|---|---|
| | 0 | | 5 µM | | 10 µM | | 50 µM | |
| Time | Average | Standard deviation | Average | Standard deviation | Average | Standard deviation | Average | Standard deviation |
| 2 h | 6 | 0 | 49 | 4 | 67 | 7 | 116 | 6 |
| 4 h | 7 | 3 | 63 | 5 | 89 | 9 | 159 | 10 |
| 6 h | 6 | 0 | 65 | 10 | 94 | 13 | 203 | 12 |
| 24 h | 9 | 3 | 120 | 5 | 129 | 3 | 291 | 17 |
| 48 h | 6 | 1 | 160 | 18 | 171 | 13 | 306 | 6 |

The best results are obtained for a concentration of 50 µM of PEI and a minimum time of incubation on the fibroblasts of 24 hours. These conditions will be retained for the screening of the molecules which stimulate the intracellular penetration. The results are statistically significant of the free probe control ($p<0.05$) for all times as from the concentration of 5 µM.

EXAMPLE 7

Analysis of the Intracellular Penetration and of the Cytotoxicity of Fluorescent Liposomes Containing 50 µM Polyethylenimine as a Function of Time The experimentation is made according to Example 6 for PEI concentrations of 0 to 100 µM. The quantification of the fluorescence is made according to Example 6. The stimulation of the intracellular penetration is expressed as a stimulation factor with respect to liposome without PEI.

The cell viability is carried out in a 96-well plate (250 µl of liposomal solution per well) by a test which evaluates the alkaline phosphatase activity on cell mats (test with paranitrophenylphosphate, n=6). The results of cell viabilities are expressed as a percentage of living cells with respect to a PEI-free fluorescent liposome control. The determination of IL1 alpha (Kit Quantikine R&D System) is done on the culture media sampled after 24 hours of incubation in parallel to a determination of total proteins (Bradford, Sigma). The results are given in Tables 6 and 7.

TABLE 6

Factor of intracellular penetration of the PFB-F and cytotoxicity as a function of time and of the concentration of PEI (n = 4 for each condition).

| Time | 0 | 5 µM | 10 µM | 50 µM | Viability PEI 50 |
|---|---|---|---|---|---|
| 2 h | 0.7 | 5.4 | 7.4 | 12.9 | 93.8% |
| 4 h | 0.8 | 7.0 | 9.9 | 17.7 | 92.4% |
| 6 h | 0.7 | 7.2 | 10.4 | 22.6 | 83.9% |
| 24 h | 1.0 | 13.3 | 14.3 | 32.3 | 72.6% |
| 48 h | 0.7 | 17.8 | 19.0 | 34.0 | 48.4% |

TABLE 7

Determination of IL1 alpha in pg/mg of total proteins

| 25 kDa PEI | 0 | 10 µM | 50 µM | 100 µM |
|---|---|---|---|---|
| Total proteins in µg/ml | 132.8 | 136.2 | 119.5 | 79.2 |
| IL1 in pg/ml | 9.2 | 12.7 | 13.1 | 14.4 |
| IL1 in pg/mg of proteins | 69.3 | 93.2 | 109.6 | 181.8 |
| Stimulation factor | 1 | 1.3 | 1.6 | 2.6 |

The results show that it is possible to increase up to 34 times the penetration factor of the fluorescent tracer in the presence of PEI in this experiment. However, it is observed that at the concentration of 50 µM of 25 kDa PEI, as from 24 hours, a non-negligible phenomenon of cytotoxicity is observed, at 48 hours, more than half of the cells are dead. As regards the synthesis of IL1 alpha at the concentration of 50 µM, the stimulation is of 1.6 times, and at 100 µM it is 2.6 times. This molecule therefore generates a stress of significant inflammatory nature.

EXAMPLE 8

Screening of Molecules which Stimulate the Intracellular Penetration of a Fluorescent Tracer Incorporated in a Liposome Liposomes are prepared with 5% of soya lecithin, 0.01% of PFB-F and 1-0.1-0.01% of molecule to be tested which is neutralised to pH 7 by hydrochloric acid if necessary in Trizma dilution buffer as described in Example 5.

55 molecules are firstly tested in triplicate, in comparison with the 50 µM 25 kDa PEI. The intracellular penetration is quantified after 24 hours of incubation on normal human fibroblasts cultivated in 24-well plates as described in Example 2. The cell viability is estimated in a 96-well plate with 200 µl of liposomal suspension. The results obtained for the concentration of 1% are given in Table 8 (Annex 2). Over the screening carried out, 15 molecules were selected since they are capable of stimulating the intracellular penetration of the fluorescent tracer by more than 10%. The cell viabilities are varied (from 37 to 99%) at a concentration of 1%. The visualisation of the fluorescent tracer confirmed the penetration for the molecules which stimulate the penetration by more than 32%. These molecules are retained in priority.

EXAMPLE 9

Influence of the Structure of the Molecules on the Stimulation of Intracellular Penetration The preparation of the liposomes with primary fatty monoamines of alkyl chain length of between 3 and 18 carbons and the quantification of the intracellular penetration of the fluorescent label are carried out as described in the preceding Example. The results are given in Table 9.

TABLE 9

Stimulation of the intracellular penetration as a function of the carbon-containing chain length

| Number of carbons Primary monoamine with a single alkyl fatty chain | STIMULATION FACTOR |
|---|---|
| 25 kDa PEI control | 34.7 |
| C3 | 0.9 |
| C4 | 1.4 |
| C6 | 0.2 |
| C7 | 3.7 |
| C10 | 39.6 |
| C11 | 95.3 |
| C12 | 47.1 |
| C13 | 44.5 |
| C14 | 11.6 |
| C15 | 14.9 |
| C18 | 19.6 |

The incorporation, in the membranes of the liposomes, of fatty amines having aliphatic chains of various sizes, shows clearly the impact of the length of the carbon-containing chains on the stimulating activity of the intracellular penetration of the PFB-F encapsulated in liposomes having 5% of lecithin. A rough classification of the fatty acids exists as a function of the length of chains. Short chains (less than 108 carbons), medium chains (from 10 to 18 carbons) and long chains (more than 18 carbons) are thus distinguished. In transposing this classification to the primary fatty amines tested within the context of this study, it appears that the medium chains are those which confer to the liposomes their property of stimulation of the intracellular penetration to the liposomes.

EXAMPLE 10

Influence of the Steric Hindrance on the Intracellular Penetration

With the view to best defining the features of the molecules having a stimulating effect on the intracellular penetration of a fluorescent tracer encapsulated in liposomes having 5% of lecithin, we have observed the impact of the steric hindrance on the potential stimulating activity of these molecules. We have thus studied the intracellular penetration of the PFB-F encapsulated in liposomes in the presence of primary fatty monoamines on the one hand, and with secondary fatty monoamines on the other hand. The preparation of the liposomes with primary or secondary fatty amines and the quantification of the intracellular penetration of the fluorescent markers are carried out as described in Example 8. The results are given in Table 10. The diamines do not enable a better intracellular penetration of the marker.

TABLE 10

Stimulation of the intracellular penetration as a function of the carbon-containing chain number

| Number of alkyl chains of the amine (chain length) | Stimulation factor |
|---|---|
| 25 KDa PEI | 34.7 |
| 1(C4) | 1.7 |
| 2(C4) | 0.7 |
| 1(C10) | 39.6 |
| 2(C10) | 1.2 |

EXAMPLE 11

Influence of the Steric Hindrance on the Intracellular Penetration

In proceeding as described notably in Example 9 or 10, it was shown that the length of the carbon-containing chain is however not the sole factor which intervenes in the stimulation of the intracellular penetration of the liposomal content.

In fact, in making the comparison of the chemical structures given in the following Figure encapsulated in liposomes, a specificity of the R group is shown which interferes with the $C_{12}$ carbon-containing chain.

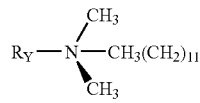

Molecule Y: Lauryldimonium hydroxypropyl hydrolysed soy protein

Stimulation factor: 38.8

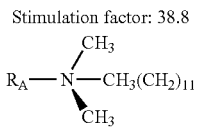

Molecule A: Lauryldimonium hydroxypropyl hydrolysed wheat protein

Stimulation factor: 6.2

$R_Y$ represents the hydrolysed and hydroxypropylated soya protein
$R_A$ represents the hydrolysed and hydroxypropylated wheat protein The quaternised molecules Y and A are products which are very common to the person skilled in the art. The steric hindrance of the quaternised molecule (commercial molecules) incorporated plays a role in the stimulation of the intracellular penetration of the liposomes having lecithin.

The molecules of the following classes (Table 11) can be, for example, used at 1% for stimulating the intracellular penetration at varying degrees up to +39%. Other quaternised hydrolysates of molecules extracted from almonds, peas, potato, or alga can also be used.

| Examples of commercially available quaternised molecules | Chemical name | Examples of potential providers |
|---|---|---|
| wheat | Cocodimonium, steardimonium, hydroxypropyltrimonium or Lauryldimonium hydrolyzed wheat protein Wheat germ-amidopropalkonium chloride | Croda |
| Soya | Lauryldimonium hydroxypropyl hydrolyzed soya protein, | Croda |
|  | Cocodimonium hydroxypropyl hydrolyzed soya protein, hydroxypropyl trimethyl ammonium chloride hydrolyzed soya protein Soy dihydroxypropyldimonium glucoside | RITA corporation |
| Keratin | Hydroxypropyltrimonium hydrolyzed keratin | RITA corporation |
| Casein | Hydroxypropyltrimonium hydrolyzed casein | RITA corporation |
| Collagen | Hydroxypropyltrimonium hydrolysed collagen, | RITA corporation |
|  | Lauryldimonium hydroxypropyl hydrolyzed collagen | Cognis |
| Silk | Hydroxypropyltrimonium hydrolyzed silk | RITA corporation |
| Rice | Cocodimonium hydroxypropyl hydrolyzed rice protein | Sochibo |
| Guar | Hydroxypropyl guar hydroxypropyltrimonium chloride, | Meyhall |
|  | Hydroxypropyl guar hydroxypropyltrimonium chloride, Guar hydroxypropyltrimonium, | Rhodia |
| honey | Hydroxypropyltrimonium honey | ARCH |
| Cellulose | Polyquaternium 4 and 10 Polyquaternium 39 | Quimasso |

EXAMPLE 12

Optimisation of the Concentration of Functionalising Molecule (which Stimulates the Intracellular Penetration)

The stimulation of the intracellular penetration of the fluorescent tracer is optimised in testing various concentrations of functionalising molecule.

Practically, liposomes are formed with 5% of soya lecithin, 0.01% of PFB-F, and 0.5 to 2.5% of the quaternised soya solution in Trizma dilution buffer. The intracellular penetration and the cytotoxicity are evaluated as described in Example 2. The results obtained are given in Table 12.

TABLE 12

Study of the concentration of molecule which stimulates the intracellular penetration and the stimulation factor, as well as cell viability

| | Quaternised soya in % | | | | |
|---|---|---|---|---|---|
| | 0.5 | 1 | 1.5 | 2 | 2.5 |
| Stimulation factor | 0.6 | 1.6 | 38.9 | 97.2 | 99.9 |
| Cell viability (%) | 92.4 | 97.9 | 87.9 | 75.4 | 77.3 |

The intracellular penetration sought after can therefore be adjusted as a function of the concentration of functionalising agent and of the maximum cytotoxicity tolerated.

EXAMPLE 13

Inflammatory Effect Compared Between the Polyethylenimine and the Quaternised Soya Selected The stimulation of the synthesis of interleukin 1 alpha is compared between liposomes which are functionalised by 50 µM PEI and various concentrations in solution of quaternised soya.

Practically, liposomes are formed with 5% of soya lecithin, 0.01% of PFB-F, and 0.5 to 2.5% of the solution of quaternised soya or 50 µM of PEI, in Trizma dilution buffer. The IL1 alpha content is evaluated with a kit (Quantikine R&D System) as described in Example 7. A test with paranitrophenylphosphate (PNPP) is carried out in parallel in order to evaluate the number of cells per well. The results of IL1 alpha content are compared to the optical density of PNPP obtained.

The results obtained are given in Table 13.

TABLE 13

Effect of the functionalising molecules (PEI and quaternised soya) on the synthesis of interleukin 1 alpha

| | Concentration of functionalising molecule | | | | |
|---|---|---|---|---|---|
| | 50 µM PEI | 0.5% soya | 1% soya | 1.5% soya | 2% soya |
| PNPP | 72.3 | 91.8 | 91.6 | 87.5 | 88.4 |
| IL1 alpha | 350 | 137.5 | 137.5 | 212.5 | 187.5 |
| IL1 alpha/PNPP | 484.1 | 149.8 | 150.1 | 242.9 | 212.1 |

The results obtained show that the solution of quaternised soya selected previously induces a cytotoxicity and an inflammatory stress which is very limited with respect to the reference molecule PEI.

EXAMPLE 14

Apoptotic Effect Compared Between the Polyethylenimine and the Quaternised Soya Selected The stimulation of the synthesis of interleukin 1 alpha is compared between liposomes which are functionalised by 50 µM PEI and various concentrations in solution of quaternised soya.

Practically, liposomes are formed with 5% of soya lecithin, 0.01% of PFB-F, and 0.5 to 2.5% of the solution of quaternised soya or 50 µM of PEI, in Trizma dilution buffer. The content of caspase 1 is evaluated with a kit (Caspase-1 Colorimetric Assay R&D System). A test with paranitrophenylphosphate (PNPP) is carried out in parallel in order to evaluate the number of cells per well. The results of caspase-1 content are compared to the optical density of PNPP obtained. The results obtained are given in Table 14.

TABLE 14

Effect of the functionalising molecules on the content of caspase-1

| | Concentration of functionalising molecule | | | | |
|---|---|---|---|---|---|
| | 50 µM PEI | 0.5% soya | 1% soya | 1.5% soya | 2% soya |
| PNPP | 59.8 | 91.8 | 91.6 | 87.5 | 88.5 |
| Caspase-1 | 642.8 | 76 | 87.7 | 78.3 | 117.5 |
| Caspase-1/PNPP | 1074.9 | 82.8 | 95.7 | 89.5 | 132.8 |

The results obtained show that the solution of quaternised soya selected previously induces a cytotoxicity and an apoptotic stress which is excessively limited with respect to the reference molecule PEI.

EXAMPLE 15

Observation of the Structure of the Liposomal Composition of Example 14 by Transmission Electronic Microscopy The liposomes prepared with 2% of quaternised soya solution, without addition of active principle and of fluorescent tracer, were observed by transmission electronic microscopy. A negative coloration of the liposomes is made by using heavy metal salts which burst between the bilayers of the multilamellar vesicles. The observation is made with a Philips CM120 transmission electronic microscope and an enlargement of 30 to 60,000.

The observation reveals the presence of concentric lipid layers which are characteristic of multilamellar structures. The average size of the liposomes observed varies from 150 to 250 nm.

EXAMPLE 16

Stimulation of the Anti-radical Protection by the Use of a Solution of Quaternised Soya of Example 11

Liposomes are prepared with 5% of soya lecithin, 0.2% of natural vitamin E and 2% of quaternised soya solution of Example 11 (molecule Y).

Practically, 0.4 g of natural vitamin E is added to 10 g of soya lecithin and 10 ml of 96% ethanol. The solution is evaporated for one night under magnetic agitation at ambient temperature and in the absence of light. After evaporation of the ethanol, 100 ml of deionised water are added. The mixture is agitated up to complete dissolution.

The liposomes are then prepared by adding 5 ml of the lecithin-vitamin E solution, 190 µl (i.e. 2%) of quaternised soya solution and 4.80 ml of 55 mM Trizma dilution buffer—27 mM NaCl adjusted to pH 5 are mixed under magnetic stirring in the absence of light for 30 minutes. The solution is then homogenised at maximum speed for 10 minutes in order to form the modified liposomes. The same solution is prepared without passing to the homogenisation and will serve a free vitamin E control.

The natural vitamin E-based liposomes are prepared in the presence of 10 µM 25 kDa PEI, so as to prevent the cytotoxicity and also without functionalising agent.

Normal human fibroblasts are sown in 24-well plates and are cultivated up to confluence. After three rinses with pH 7.4 phosphate buffer with calcium and magnesium (Invitrogen), the various solutions are incubated diluted to the half (i.e. final vitamin E concentration of 0.1%) in culture medium for at least two hours. Wells are incubated with culture medium alone and will serve as probe control in the following. After three rinses in pH 7.4 phosphate buffer with calcium and magnesium so as to remove the liposomes and the free vitamin E, the cell mats are incubated in the presence of Dihydrorhodamine 123 (Molecular Probes) at the rate of 200 µl/well of a solution prepared as follows: 150 µl of a 1 mM solution dissolved in 15 ml of HBSS buffer. The plate is read for fluorescence at 490-530 nm, and then irradiated at 0.8 J/cm$^2$ with UVB at 912 nm, and is then read again for fluorescence at the same wavelengths. The results are expressed as ratios:
A=irradiated/non-irradiated (I/NI)
B=(I/NI liposome)/(I/NI probe control)
C=liposomed Vitamin E/free vitamin E.

The fluorescent probe used enables the presence of intracellular reactive oxygen intermediates to be evaluated since it diffuses passively through the cell membranes wherein it can then be oxidised to cationic rhodamine. The fluorescent probe reacts positively for example with hydrogen peroxide and peroxynitrites. The results obtained are given in Table 15.

TABLE 15

Anti-radical protection by the thus-modified liposomes

|  | I | NI | A = I/NI | B = liposome/ control | C = liposome/free |
|---|---|---|---|---|---|
| Product of the invention | 118990 | 58786 | 2.01 | 79.3% | +23% |
| Non-functionalised liposome | 114907 | 52306 | 2.31 | 91.1% | +11% |
| Liposome PEI | 105257 | 40148 | 2.82 | 111.4% | −9% |

These results indicate that the liposomes functionalised by the quaternised soya protein enable obtaining more than 20% of protective effect against radical stress with respect to non-functionalised liposomes, whereas the liposomes functionalised with the reference molecule PEI do not enable a protective effect to be observed on the one hand, they even generate an additional stress.

EXAMPLE 17

Stimulation of Depigmentation by the Products of the Invention

Liposomes were prepared according to the following protocol: 5% of soya lecithin to which 2% of quaternised soya solution or 10 µM PEI is added or not. Actives are also co-encapsulated: Phytolight® (Coletica, Lyons, France) without 0.05% preservative (cocktail of plant actives), 0.05% arbutine and 1 mM catechin (Sigma). The molecules were applied free, in 5% lecithin liposome, in 10 µM PEI functionalised liposomes or 2% quaternised soya, on normal human melanocytes cultivated in 24-well plates and pre-confluent. The actives which are liposomed or not are incubated for 66 hours at 37° C. under 5% $CO_2$ in MMK2 medium (Sigma). After 3 rinses with phosphate buffer with calcium and magnesium (Invitrogen), extraction into phosphate buffer containing 0.5% triton X-100, the tyrosinase activity is quantified by a determination in the presence of L-DOPA and MBTH (3-methyl-2-benzothiazolinone hydrazone). The formation of a MBTH-o-quinone compound is characterised by an absorbance value at 490 nm quantified kinetically. The tyrosinase activity is expressed by the slope (rate) of the enzymatic reaction. The results are given in Table 16.

TABLE 16

Depigmenting effect of liposomed or non-liposomed actives (expressed in rate of enzymatic reaction)

|  | Free | Liposome | PEI Liposome | Soya liposome |
|---|---|---|---|---|
| Arbutin | 0.004 | 0.001 | 0 | 0 |
| Phytolight ® | 0.01 | 0.008 | 0.003 | 0.0016 |
| Catechin | 0.007 | 0.007 | 0 | 0.003 |

These results show that as a function of the actives co-encapsulated, the functionalisation enables an increase in the inhibition of the tyrosinase activity in vitro on normal human melanocytes. The functionalisation by the quaternised soya is more effective than that obtained by addition of PEI for the complex of plant extracts, equivalent for arbutin and slightly less for catechin. In every case, the activity is at least 2.3 times greater than with a non-functionalised liposome.

EXAMPLE 18

Method of Decreasing the Size of the Products of the Invention

The size of the liposomes can be decreased by use of a high pressure homogeniser (working pressure of greater than 1,000 bars, preferably greater than 2,000 bars, more preferably greater than 3,000 bars). At 3,000 bars, this instrument enables liposomes of about 50 nm to be obtained.

The size of the liposomes was analysed with the aid of a laser particle size analyser (Beckman Coulter, N4 plus, Submicron Particle Size Analyser) and by transmission electronic microscopy, as described in Example 15.

EXAMPLE 19

Demonstration of the Penetration of Material which is Carried by the Products of the Invention after Transcutaneous Permeation: Examples with a Fluorescent Tracer, Vitamin E or Genetic Material The penetration of fluorescent molecule (0.01% PFP-F), free or incorporated in a liposome as described in Example 12, comprising or not comprising 2% quaternised soya solution selected in Example 11, was quantified by transcutaneous permeation on human skin. The diffusion kinetics were quantified by spectrofluorimetry from 3 to 24 hours. The release was quantified after 24 additional hours. The storage was also evaluated last. The number of samples tested is 5 per condition. The results obtained given in Table 17 show that the use of liposomes prepared in the presence of quaternised soya significantly stimulate the diffusion, the release and the storage of the fluorescent tracer with respect to the non-vectorised form or form vectorised without quaternised agent.

TABLE 17

|  | Free | Liposome | Quaternised liposome |
|---|---|---|---|
| Diffusion | 0.57 ± 0.03 | 1.17 ± 0.05 | 1.76 ± 0.13 |
| Release 24 h | 0.691 ± 0.06 | 1.398 ± 0.07 | 1.77 ± 0.21 |
| Storage | 0.81 ± 0.1 | 1.27 ± 0.17 | 2.61 ± 0.33 |

The penetration of vitamin E molecule (0.5%), free or incorporated in a liposome as described in Example 12, comprising or not 2% quaternised soya solution selected in Example 11, was quantified by transcutaneous permeation on human skin. The diffusion kinetics were quantified by high performance liquid chromatography from 5 to 24 hours. The release was quantified after 24 additional hours. The storage was also evaluate last. The results obtained also show that the use of liposomes prepared in the presence of quaternised soya significantly stimulates the diffusion, the release and the storage of the vitamin E with respect to the non-vectorised form or form vectorised without quaternised agent.

The same experiment of transcutaneous penetration was carried out with the incorporation or not of fluorescent genetic material (200 mM) in a liposome as described in Example 12 in the presence of a 2% soya solution. The results obtained by observation by epifluorescence optical microscopy of transverse sections of the skin show that the use of liposomes prepared in the presence of quaternised soya enable the diffusion of the genetic material to the deep dermis.

Sequence of the fluorescent probe of duplexed elastin 19-20:

```
Sense:      5'-(FITC) AGCUGCUAAGGCUGGCGCUTT-3'
anti-sense: 5'-AGCGCCAGCCUUAGCAGCUTT-3'
```

EXAMPLE 20

Use of the Products of the Invention in Oil-in-water Emulsion Type Cosmetic or Pharmaceutical Formulations Formulation 20a

| A | Water | qsp 100 |
|---|---|---|
|  | Butylene Glycol | 2 |
|  | Glycerine | 3 |
|  | Sodium Dihydroxycetyl Phosphate, | 2 |
|  | Isopropyl Hydroxycetyl Ether |  |

-continued

| B | Glycol Stearate SE | 14 |
|---|---|---|
|  | Triisononaoin | 5 |
|  | Octyl Cocoate | 6 |
| C | Butylene Glycol, Methylparaben, Ethylparaben, Propylparaben, pH adjusted to 5.5 | 2 |
| D | Products of the invention | 0.01–10% |

Formulation 20b:

| A | Water | qsp 100 |
|---|---|---|
|  | Butylene Glycol | 2 |
|  | Glycerine | 3 |
|  | Polyacrylamide, Isoparaffin, Laureth-7 | 2.8 |
| B | Butylene Glycol, Methylparaben, Ethylparaben, Propylparaben; Butylparaben, Phenoxyethanol, | 2 |
| C | Products of the invention | 0.01–10% |

Formulation 20c:

| A | Carbomer | 0.50 |
|---|---|---|
|  | Propylene Glycol | 3 |
|  | Glycerol | 5 |
|  | Water | qsp 100 |
| B | Octyl Cocoate | 5 |
|  | Bisabolol | 0.30 |
|  | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01–10% |

These formulations 20a, 20b and 20c are manufactured as usual, namely, each group of components A, B, etc. is homogenized separately and then the following group of components is admixed therewith. Thus, group of components B is admixed with component A, afterwards, group of components C is added to the mixture of components A plus B, and so on, as is well understood by those skilled in the art to which the invention pertains.

This procedure is also applied for any other similar invention's examples like those set forth here below.

EXAMPLE 21

Use of the Products of the Invention in a Water-in-oil Type Formulation

| A | PEG 30 - dipolyhydroxystearate | 3 |
|---|---|---|
|  | Capric Triglycerides | 3 |
|  | Cetearyl Octanoate | 4 |
|  | Dibutyl Adipate | 3 |
|  | Grape Seed Oil | 1.5 |
|  | Jojoba Oil | 1.5 |
|  | Phenoxyethanol, Methylparaben, Propylparaben, Butylparaben, Ethylparaben | 0.5 |

-continued

| | | |
|---|---|---|
| B | Glycerine | 3 |
| | Butylene Glycol | 3 |
| | Magnesium Sulfate | 0.5 |
| | EDTA | 0.05 |
| | Water | qsp 100 |
| C | Cyclomethicone | 1 |
| | Dimethicone | 1 |
| D | Perfume | 0.3 |
| E | Products of the invention | 0.01–10% |

EXAMPLE 22

Use of the Products of the Invention in a Triple Emulsion Type Formulation

| | Primary emulsion W1/O | |
|---|---|---|
| A | PEG 30 - dipolyhydroxystearate | 4 |
| | Capric Triglycerides | 7.5 |
| | Isohexadecane | 15 |
| | PPG-15 Stearyl ether | 7.5 |
| B | Water | 65.3 |
| C | Phenoxyethanol, Methylparaben, Propylparaben, Butylparaben, Ethylparaben | 0.7 |
| | Secondary emulsion W1/O/W2 | |
| A | Primary emulsion | 60 |
| B | Poloxamer 407 | 2 |
| | Phenoxyethanol, Methylparaben, Propylparaben, 2-bromo-2nitropropane-1,3 diol | 0.3 |
| | Water | qsp 100 |
| C | Carbomer | 15 |
| D | Triethanolamine | PH 6.0–6.5 |
| E | Products of the invention | 0.01–10% |

EXAMPLE 23

Use of the Products of the Invention in a Formulation of Lipstick Type and Other Anhydrous Products

| | | |
|---|---|---|
| A | Mineral Wax | 17.0 |
| | Isostearyl Isostearate | 31.5 |
| | Propylene Glycol Dipelargonate | 2.6 |
| | Propylene Glycol Isostearate | 1.7 |
| | PEG 8 Beeswax | 3.0 |
| | Hydrogenated Palm Kernel Oil Glycerides, Hydrogenated Palm Glycerides | 3.4 |
| | Lanolin Oil | 3.4 |
| | Sesame Oil | 1.7 |
| | Cetyl Lactate | 1.7 |
| | Mineral Oil, Lanolin Alcohol | 3.0 |
| B | Castor Oil | qsp 100 |
| | Titanium Dioxide | 3.9 |
| | CI 15850: 1 | 0.616 |
| | CI 45410: 1 | 0.256 |
| | CI 19140: 1 | 0.048 |
| | CI 77491 | 2.048 |
| C | Products of the invention | 0.01–5% |

EXAMPLE 24

Use of the Products of the Invention in a Formulation of Aqueous Gels (Eyeliners, Slimmers, etc.)

| | | |
|---|---|---|
| A | Water | qsp 100 |
| | Carbomer | 0.5 |
| | Butylene Glycol | 15 |
| | Phenoxyethanol, Methylparaben, Propylparaben, Butylparaben, Ethylparaben | 0.5 |
| B | Products of the invention | 0.01–10% |

EXAMPLE 25

Preparation of Pharmaceutical Formulations Containing the Product of the Invention Formulation 25a: Preparation of Tablets

| | | |
|---|---|---|
| A | Excipients | in g per tablet |
| | Lactose | 0.359 |
| | Sucrose | 0.240 |
| B | Product of the invention | 0.001–0.1 |

Formulation 25b: Preparation of an Ointment

| | | |
|---|---|---|
| A | Excipients | |
| | Low density polyethylene | 5.5 |
| | Liquid paraffin | qsp 100 |
| B | Product of the invention | 0.001–0.1 |

Formulation 25c: Preparation of an Injectable Formula

| | | |
|---|---|---|
| A | Excipient | |
| | Saline isotonic solution | 5 ml |
| B | Product of the invention | 0.001–0.1 g |

Phase A and phase B are packaged in separate ampoules and are mixed prior to use.

EXAMPLE 26

Evaluation of the Cosmetic Acceptation of the Products of the Invention

Toxicology tests were carried out on the compounds obtained according to Example 15 (without incorporation of active principle), by a skin and ocular evaluation in the rabbit, by the study of the absence of abnormal toxicity by single oral administration in the rat and by the study of the sensitising power in the guinea pig.

Evaluation of the Primary Irritation of the Skin in the Rabbit:

The preparations described above were applied without dilution at the dose of 0.5 ml on the skin of 3 rabbits according to the method recommended by the OECD in relation to the study of "the acute irritant/corrosive effect on the skin".

The products are classed according to the criteria defined in the Decision of Jan. 2, 1982 published in the Official Journal of the French Republic (the "JORF") of Feb. 21, 1982.

The results of these tests have enabled concluding that the preparation containing the compound obtained according to Example 12 was non-irritant for the skin.

Evaluation of the Ocular Irritation in the Rabbit:

The preparations described above were instilled pure and in one batch at the rate of 0.1 ml in the eye of three rabbits according to the method recommended by the directive of the OECD NO. 405 of Feb. 24, 1987, in relation to the study of "the acute irritant/corrosive effect on the eyes".

The results of this test enable concluding that the preparations can be considered as non-irritant for the eyes.

Test on the Absence of Abnormal Toxicity by Single Oral Administration in the Rat:

The preparations described were administered in one batch orally at the dose of 5 g/Kg of body weight, to 5 male rats and 5 female rats according to a protocol inspired from the Directive of the OECD No. 401 of Feb. 24, 1987 and adapted to cosmetic products.

The LD0 and LD50 are found to be greater than 5,000 mg/Kg. The preparations tested are therefore not classed amongst the preparations which are dangerous by ingestion.

Evaluation of the Skin Sensitisation Potential in the Guinea Pig:

The preparations described are subjected to the maximization test described by Magnusson and Kligmann, a protocol which is in agreement with the directive line No. 406 of the OECD. The preparations are classed as non-sensitising by contact with the skin.

Evaluation of the Mutagenicity Potential:

The protocol is in accordance with the directive line of the OECD No. 471 (Directive 92/69/EEC).

The mutagenesis tests were carried out on <<*Salmonella typhimurium*>> and on <<*Escherichia coli*>> according to the method of Ames et al. (*Mutation Research*, 1975, 31, 347-364). Five strains were exposed to the product of the invention in minimum medium, with or without exogenous systems of metabolism activation (so as to distinguish pro-mutagens and mutagens directly). After incubation, the mutated colonies were counted and were compared to the number of colonies spontaneously mutated amongst the controls.

The product of the invention does not possess any mutagenic activity in the sense of Directive 92/69 EEC.

Evaluation of the Sensitisation Potential on Healthy Volunteers:

Evaluation on a panel of volunteers of the allergising potential of the product of the invention. The protocol is in accordance with the method of Marzulli and Maibach (*Contact Dermatitis*, 1976, 2, 1-17) which comprises an induction phase and a triggering test. This test is made on a panel of 100 healthy volunteers of feminine and/or masculine sex, aged between 18 and 65 and having any skin type.

An occlusive patch containing the product of the invention diluted to 20% was applied on the scapular zone of each one of the volunteers. The patches were left in direct contact with the skin for 24 hours and were reapplied every two days for 3 weeks for a total of 9 applications. After the removal of each patch, the clinical signs of irritation and of the skin sensitisation were evaluated=Induction Phase.

After a period of 2 weeks, other patches containing the product of the invention diluted to 20% were applied on the skin of the volunteers and were left in direct contact with the skin surface for 24 hours. The clinical signs of the irritation and of the skin sensitisation were evaluated 24, 48 and 72 hours after the removal of the patch="Challenge" Phase.

None of the 100 volunteers involved in the study presented clinical signs of irritation or of skin sensitisation, whether it be during the induction phase or the "challenge" phase.

Under the experimental conditions retained, the product of the invention diluted to 20% is devoid of allergising potential.

TABLE 1

Selection of fluorescent probes as tracers

| Probe name | Chracteristics | Exc/Em | Concentration | Encapsulated | leak | cell-permeating | Toxicity | Penetration in liposome | Retained |
|---|---|---|---|---|---|---|---|---|---|
| #L7545L Lysosensor yellow/blue DND 160 | pH sensitive | 329/440 | 10 µM | Yes | Yes | Yes | No | No | No |
| #H-348 hydroxypyrene trisulfonic acid, trisodium salt | | 403/511 | 1 mM | No | NT | No | NT | No | No |
| #P-12925 pentafluorobenzoylamino fluorescein | | 492/516 | 200 µM | Yes | No | No | | Yes | Yes |
| #F-1200 Fura-2. pentapotassium salt | Sensitive to $Ca^{2+}$ | 335/505 | 10 µM | No | | No | No | No | Yes |
| #C-369 carboxy dichlorofluorescein | Fluoresces if esterases | | 85 µM | Yes | Yes | Yes | NT | NT | No |
| #B-1151 carboxyethyl carboxyffluorescein | | 482/520 | 50 µM | No | NT | ? | NT | NT | No |
| #T-490 tetramethylrhodamine isothiocyanate TRITC | | 555/580 | | Yes | ? | ? | No | Yes | No Interferes with PEI |
| #C-687 cascade blue hydrazine trisodium salt | | 399/421 | 200 µM | Yes | NT | No | No | Very low | No |
| #S-1129 sulfo fluorescein diacetate | | | 200 µM | NT | NT | no | No | Very low | No |
| #D-3329 dextran texas red | | 592/609 | | NT | NT | No | Yes | No | No |

Annex 2: Results of screening of molecules which stimulate the penetration (Table 8)

| INCI name | Stimulation factor | Viability | Visualisation |
|---|---|---|---|
| Polyethylenimine 25 kDa | 34.7 | 74.1 | + |
| Cocodimonium hydroxypropyl hydrolyzed wheat protein | 4.3 | 86 | − |
| Cocodimonium hydroxypropyl hydrolyzed rice protein | 18 | 85 | − |
| Steardimonium hydroxypropyl hydrolyzed wheat protein | 4.6 | 86.4 | − |
| Lauryldimonium hydroxypropyl hydrolyzed wheat protein | 6.2 | 87.5 | − |
| Hydroxypropyltrimonium hydrolyzed wheat protein | 1.3 | 91.7 | − |
| Hydroxypropyltrimonium honey | 15 | 92 | − |
| Sodium lauroyl Oat amino acids | 0.8 | 76.6 | − |
| Sodium lauroyl wheat amino acids | 1.1 | 46.1 | − |
| Cocoamine | 32.7 | 79.7 | + |
| Lauryldimonium hydroxypropyl hydrolyzed soya protein | 38.8 | 87.9 | + |
| Chitosan | 10.3 | 99 | − |
| Hydroxypropyl guar hydroxypropyltrimonium chloride | 1.1 | 74.8 | − |
| Hydroxypropyl guar | −0.2 | 91.1 | − |
| Hydroxypropyl guar | −0.4 | 97.5 | − |
| Hydroxypropyl guar hydroxypropyltrimonium chloride | 1.4 | 71.2 | − |
| Guar hydroxypropyltrimonium | 0.6 | 53.3 | − |
| Meypro | 1 | 91.6 | − |
| Polyquaternium 7 | 0.3 | 80.1 | − |
| Polyvinylpyrrolidone (1) | 1.4 | 85.1 | − |
| polyvinylcaprolactam | 4.1 | 0 | − |
| Polyvinylpyrrolidone (2) | 0.7 | 26.6 | − |
| Polyvinylpyrrolidone (3) | 0.7 | 71 | − |
| Polyquaternium 16 (1) | 4.6 | 83.5 | − |
| Polyquaternium 11 (1) | 1.5 | 49.7 | − |
| Cocotrimonium methosulfate | 0.1 | 55 | − |
| Polyquaternium 16 (2) | 8.4 | 33.8 | − |
| Polyquaternium 16 (3) | 1 | 38.8 | − |
| Polyquaternium 16 (4) | 12.5 | 67.1 | − |
| Polyquaternium 16 (5) | 0.2 | 85.3 | − |
| Polyquaternium 44 | 0.8 | 59.7 | − |
| Cocoalkonium chloride | 5.6 | 36.3 | − |
| Cocotrimonium chloride | −0.2 | 65.6 | − |
| Tetrahydroxypropyl ethylenediamine | 1.9 | 95.3 | − |
| Stearamidopropyl cetearyl dimonium tosylate and PG | 13.1 | 93.2 | − |
| Quaternium 70 and PG | −0.2 | 63.9 | − |
| Quaternium 26 | 30.9 | 59.2 | − |
| Quaternium 22 | 2 | 98.9 | − |
| Polyquaternium 28 | 0.6 | 79.3 | − |
| Polyquaternium 11 (2) | 2.9 | 50.7 | − |
| Polyquaternium 11 (3) | 2.9 | 77.1 | − |
| Polyquaternium 2 | 4.2 | 23.6 | − |
| Stearalkonium chloride | 17.6 | 37.4 | − |
| Propylamine C3 | 0.9 | 103.3 | − |
| n-Butylamine C4 | 1.4 | 106.2 | − |
| Dibutylamine 2 C4 | 0.7 | 75.7 | − |
| Hexylamine C6 | 0.2 | 82.1 | − |
| Heptylamine C7 | 3.7 | 39.4 | − |
| Dioctylamine 2 C8 | 1 | 34.7 | − |
| Decylamine C10 | 39.6 | 68.5 | + |
| Didecylamine 2 C10 | 1.2 | 28.3 | − |
| Undecylamine C11 | 95.3 | 84 | + |
| Dodecylamine C12 | 47.1 | 57 | + |
| Tridecylamine C13 | 44.5 | 62.6 | + |
| Tetradecylamine C14 | 11.6 | 54.8 | − |
| Pentadecylamine C15 | 14.9 | 73 | − |
| Octadecylamine C18 | 19.6 | 61.2 | − |
| Oleylamine C18:1 | 1.9 | 87.1 | − |

What is claimed is:

1. Hydrated lamellar phases or liposomes, comprising at least in part in their structure a substance or a mixture of substances which is (are) capable of stimulating the intracellular penetration of at least one active principle present or carried in said hydrated lamellar phases or liposomes and is (are) selected from the group consisting of:
   a) a primary, secondary, tertiary, or quaternary fatty monoamine of carbon-containing chain length of between C10 and C13; and
   b) a quaternised soya protein of formula R—N($R_1R_2R_3$), in which R symbolizes the plant protein molecule, which is hydrolysed or not, hydroxypropylated; $R_1$ and $R_2$ independently being a C1-C6 hydrocarbon group, and $R_3$ being an alkyl radical having 10 to 18 carbon atoms,
   and wherein the lamellar phases or liposomes comprise at least one polar lipid or a polar sphingolipid.

2. The lamellar phases or liposomes of claim 1, wherein the lamellar phases or liposomes further comprise at least one agent which modifies the membrane of liposomes in the lipid phase.

3. The lamellar phases or liposomes of claim 2, wherein said membrane modifying agent comprises a polar lipid selected from the group consisting of a triglyceride, a polar phospholipid, a polar sphingolipid, and any mixture thereof.

4. The lamellar phases or liposomes of claim 3, wherein the polar phospholipid is selected from phosphatidylcholine or lecithin, phosphatidylethanolamine or cephaline, phosphatidylserine, phospharidylglycerol, diphosphatidylglycerol, or cardiolipin, phosphatidylinositol, and any mixture thereof.

5. The lamellar phases or liposomes of claim 3, wherein the polar sphingolipid is selected from a ceramide, a sphingophospholipid, a glycosphyngolipid, and any mixture thereof.

6. The lamellar phases or liposomes of claim 1, wherein the lamellar phases or liposomes comprise at least one lecithin extracted from a natural source selected from the group consisting of soya, rape, sunflower, lupin, groundnut, sesame, marrow, bran oil, bigseed falseflax, calendula, flax, hemp, and any mixture thereof.

7. The lamellar phases or liposomes of claim 1, wherein the lamellar phases or liposomes comprise cholesterol or cholesterylhemisuccinate as an agent which rigidifies the membranes.

8. The lamellar phases or liposomes according to claim 1, wherein the concentration of the substance or the mixture of substances which stimulate(s) the intracellular penetration ranges between 0.05% and 25% by weight of a composition which contains the hydrated lamellar phases or liposomes.

9. The lamellar phases or liposomes of claim 1, wherein the concentration of the substance or the mixture of substances which stimulate(s) the intracellular penetration ranges between 0.5% and 2.5% by weight of a composition which contains the hydrated lamellar phases or liposomes.

10. The lamellar phases or liposomes of claim 1, wherein the substance or the mixture of substances is a quaternised soya protein of formula R—N($R_1R_2R_3$), in which R symbolizes the plant protein molecule, which is hydrolysed or not, hydroxypropylated; $R_1$ and $R_2$ independently being a C1-C6 hydrocarbon group, and $R_3$ being an alkyl radical having 10 to 18 carbon atoms.

11. The lamellar phases or liposomes of claim 1, wherein $R_3$ is lauryl.

12. The lamellar phases or liposomes of claim 1, wherein $R_3$ is an alkyl radical having 10 to 13 carbon atoms.

13. The lamellar phases or liposomes of claim 1, wherein the at least one active principle is selected from the group consisting of an anti-radical agent, a depigmenting agent, a slimming agent, a skin or hair pigmenting agent, and any mixture thereof.

14. The lamellar phases or liposomes of claim 13, wherein the anti-radical agent is selected from the group consisting of vitamin E, a flavonoid, a carotenoid, vitamin C, and any mixture thereof.

15. A cosmetic, dermocosmetic, pharmaceutical or dermopharmaceutical composition, comprising lamellar phases or liposomes which comprise at least one substance which stimulates intracellular penetration as defined in claim 1, in admixture with a cosmetically or pharmaceutically acceptable excipient.

16. The composition of claim 15, wherein the concentration of the substance which stimulates intracellular penetration ranges between 0.05% and 25% by weight of the final composition.

17. The composition of claim 16, wherein the concentration of the substance which stimulates intracellular penetration ranges between 0.5 and 2.5% by weight of the final composition.

18. A cosmetic or dermocosmetic composition having an anti-wrinkle effect, an antioxidant effect, a slimming effect, a skin paling effect, or a skin or hair pigmenting effect, comprising the hydrated lamellar phases or liposomes as defined in claim 1, wherein the lamellar phases or liposomes comprise the substance or the mixture of substances at a concentration of from 0.05% to 25% by weight of a final composition, in admixture with a cosmetically acceptable excipient.

19. A method of cosmetic care, comprising applying onto zones of skin or hair in need thereof the cosmetic or dermocosmetic composition as defined in claim 15.

20. The method of claim 19, wherein the cosmetic care is selected from the group consisting of an anti-wrinkles care, an antioxidant care, a slimming care, a skin paling care, and a skin or hair pigmenting care.

21. Liposomes, comprising:
   a) at least one active principle present or carried in said liposomes;
   b) polar phospholipid; and
   c) at least in part in their structure, a substance or a mixture of substances stimulating the intracellular penetration of the at least one active principle, wherein the substance or the mixture of substances comprises a cationic natural polymer or a natural polymer rendered cationic, selected from the group consisting of quaternised soya proteins of formula R—N($R_1R_2R_3$), in which R symbolizes the plant protein molecule, which is hydrolysed or not, hydroxypropylated; $R_1$ and $R_2$ independently being a C1-C6 hydrocarbon group, and $R_3$ being an alkyl radical having 10 to 18 carbon atoms.

22. The liposomes of claim 21, wherein the substance or the mixture of substances comprises a quaternised soya protein of formula R—N($R_1R_2R_3$), in which R symbolizes the plant protein molecule, which is hydrolysed or not, hydroxypropylated; $R_1$ and $R_2$ independently being a C1-C6 hydrocarbon group, and $R_3$ being an alkyl radical having 10 to 13 carbon atoms.

23. The liposomes of claim 21, wherein the substance or the mixture of substances is lauryldimonium hydroxypropyl hydrolysed soya protein.

24. The liposomes of claim 21, wherein the substance or the mixture of substances is cocodimonium hydroxypropyl hydrolyzed soya protein.

25. Hydrated lamellar phases or liposomes, comprising at least in part in their structure a substance or a mixture of substances which is (are) capable of stimulating the intracellular penetration of at least one active principle present or carried in said hydrated lamellar phases or liposomes and is (are) selected from the group consisting of:
- a) a primary, secondary, tertiary, or quaternary fatty monoamine of carbon-containing chain length of between C10 and C13; and
- b) a quaternised plant protein of formula R—N(R1R2R3), in which R symbolizes the plant protein molecule, which is hydrolysed or not, hydroxypropylated; R1 and R2 independently being a C1-C6 hydrocarbon group, and R3 being an alkyl radical having 10 to 18 carbon atoms, wherein the hydrated lamellar phases or liposomes are prepared by:
- i) preparing a hydro-lipidic mixture comprising at least one polar lipid or a polar sphingolipid, wherein the hydro-lipidic mixture is capable of forming said hydrated lamellar phases or liposomes in a dispersion process; and
- ii) incorporating, before or during the dispersion process of the hydro-lipidic mixture, the substance or the mixture of substances to the hydro-lipidic mixture.

26. The hydrated lamellar phases or liposomes of claim 25, wherein the substance or the mixture of substances is a quaternised soya protein of formula R—N(R1R2R3), in which R symbolizes the plant protein molecule, which is hydrolysed or not, hydroxypropylated; R1 and R2 independently being a C1-C6 hydrocarbon group, and R3 being an alkyl radical having 10 to 18 carbon atoms.

27. The hydrated lamellar phases or liposomes of claim 25, wherein the substance or the mixture of substances is lauryldimonium hydroxypropyl hydrolysed soya protein.

28. The hydrated lamellar phases or liposomes of claim 25, wherein the substance or the mixture of substances is cocodimonium hydroxypropyl hydrolyzed soya protein.

29. The method of cosmetic care of claim 19, wherein it is a method of skin care and wherein the composition is applied onto zones of the skin.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Unknown
<220> FEATURE:
<223> OTHER INFORMATION: probe

<400> SEQUENCE: 1
agcugcuaag gcuggcgcut t           21

<210> SEQ ID NO 2
<211> LENGTH: 21
<212> TYPE: DNA
<213> ORGANISM: Unknown
<220> FEATURE:
<223> OTHER INFORMATION: probe

<400> SEQUENCE: 2
agcgccagcc uuagcagcut t           21